(12) United States Patent
Andersen et al.

(10) Patent No.: US 10,052,235 B2
(45) Date of Patent: Aug. 21, 2018

(54) LANYARD WITH INTEGRATED EAR PLUGS AND RETRACTABLE SHEATH

(71) Applicants: Cade Andersen, Kaysville, UT (US); Brian Andersen, Kaysville, UT (US)

(72) Inventors: Cade Andersen, Kaysville, UT (US); Brian Andersen, Kaysville, UT (US)

( * ) Notice: Subject to any disclaimer, the term of this patent is extended or adjusted under 35 U.S.C. 154(b) by 0 days.

(21) Appl. No.: 15/696,168

(22) Filed: Sep. 5, 2017

(65) Prior Publication Data

US 2018/0008469 A1 Jan. 11, 2018

Related U.S. Application Data

(63) Continuation of application No. 14/677,861, filed on Apr. 2, 2015, now Pat. No. 9,770,367.

(51) Int. Cl.
*A61F 11/12* (2006.01)
*A61F 9/02* (2006.01)
*G09F 3/20* (2006.01)
*A45F 5/00* (2006.01)

(52) U.S. Cl.
CPC ............. *A61F 11/12* (2013.01); *A61F 9/029* (2013.01); *A45F 2005/002* (2013.01); *A45F 2005/006* (2013.01); *A45F 2200/055* (2013.01); *A45F 2200/0541* (2013.01); *G09F 3/207* (2013.01)

(58) Field of Classification Search
CPC .. A45F 3/14; A45F 2003/14; A45F 2003/142; A45F 2003/003; A45F 2005/002; A45F 2200/0541; A45F 2200/055
USPC .......................... 224/576, 181, 607, 257, 258
See application file for complete search history.

(56) References Cited

U.S. PATENT DOCUMENTS

| 2,856,466 | A | * | 10/1958 | Gustafson | .............. | G02C 11/06 |
| | | | | | | 381/327 |
| D185,852 | S | | 8/1959 | McFayden | | |
| 3,297,832 | A | * | 1/1967 | Brown | .................... | G02C 11/06 |
| | | | | | | 181/130 |
| D212,201 | S | | 9/1968 | Grayson | | |
| D225,782 | S | | 1/1973 | King | | |
| 3,871,372 | A | | 3/1975 | Bivins | | |
| 3,943,925 | A | | 3/1976 | Leight | | |
| D262,491 | S | | 12/1981 | Ebert | | |
| 4,682,363 | A | * | 7/1987 | Goldfarb | .................. | H04B 1/44 |
| | | | | | | 381/189 |
| D291,894 | S | | 9/1987 | Weisenfeld | | |

(Continued)

OTHER PUBLICATIONS

Ebay, Official 2016 Goodwood Sky Sports F1 Lanyard Ear Plugs Canister, Sep. 2016.

(Continued)

*Primary Examiner* — Brian D Nash
(74) *Attorney, Agent, or Firm* — Pate Peterson PLLC; Brett Peterson

(57) ABSTRACT

A lanyard is provided. The lanyard may include a lanyard cord which is attached to a personal item such as safety glasses or an access card, an earplug cord which is attached to a first earplug and a second earplug, and a flexible retractable sheath. The lanyard cord and earplug cord may be disposed in the lumen of the retractable sheath and the retractable sheath is movable between a first position where it covers a first section of the lanyard cord and the earplug cord and a second position where it exposes the first section of the lanyard cord and the earplug cord.

18 Claims, 26 Drawing Sheets

(56) References Cited

U.S. PATENT DOCUMENTS

| | | | |
|---|---|---|---|
| 4,856,086 A * | 8/1989 | McCullough | A61F 9/029 455/344 |
| 4,901,355 A * | 2/1990 | Moore | A61F 9/029 381/327 |
| D309,619 S | 7/1990 | Kalbach | |
| 5,074,375 A | 12/1991 | Grozil | |
| D328,908 S | 8/1992 | Kalbach | |
| 5,159,639 A * | 10/1992 | Shannon | G02C 11/06 381/312 |
| D337,337 S | 7/1993 | Dang | |
| D338,037 S | 8/1993 | Miller | |
| 5,366,072 A | 11/1994 | Goldenberg | |
| 5,369,452 A | 11/1994 | Williams | |
| D354,759 S | 1/1995 | Wolff | |
| D354,760 S | 1/1995 | Wolff | |
| D355,358 S | 2/1995 | Starr | |
| D361,081 S | 8/1995 | Pardinas | |
| D362,261 S | 9/1995 | Bernzweig | |
| 5,475,449 A | 12/1995 | Pyle | |
| D368,272 S | 3/1996 | Starr | |
| D370,023 S | 5/1996 | Torrey | |
| D370,492 S | 6/1996 | Torrey | |
| D371,150 S | 6/1996 | Bolash | |
| D371,154 S | 6/1996 | Kalbach | |
| 5,541,677 A | 7/1996 | Huhtala | |
| 5,600,873 A | 2/1997 | May | |
| 5,606,743 A * | 2/1997 | Vogt | H04B 1/086 16/228 |
| D382,503 S | 8/1997 | Kalbach | |
| 5,655,263 A | 8/1997 | Stoller | |
| 5,781,272 A | 7/1998 | Bright | |
| D411,562 S | 6/1999 | Riley | |
| D416,038 S | 11/1999 | Kalbach | |
| D418,774 S | 1/2000 | Kalbach | |
| D420,039 S | 2/2000 | Carey | |
| D424,600 S | 5/2000 | Riley | |
| 6,067,664 A | 5/2000 | Cortes | |
| D435,265 S | 12/2000 | Landis | |
| 6,176,576 B1 | 1/2001 | Green | |
| D450,744 S | 11/2001 | Rhoades | |
| D455,772 S | 4/2002 | Rosso | |
| D455,773 S | 4/2002 | Rosso | |
| D462,523 S | 9/2002 | Kalbach | |
| D467,416 S | 12/2002 | Kalbach | |
| D486,174 S | 2/2004 | Chisolm | |
| D486,511 S | 2/2004 | Kalbach | |
| D491,364 S | 6/2004 | Vish | |
| 6,752,305 B2 | 6/2004 | Shattuck | |
| 6,764,177 B1 | 7/2004 | Chisolm | |
| 6,941,619 B2 | 9/2005 | Mackay et al. | |
| D536,364 S | 2/2007 | Kalbach | |
| 7,213,916 B1 | 5/2007 | Pettett | |
| D562,807 S | 2/2008 | Andre | |
| D576,199 S | 9/2008 | Mosley | |
| 7,594,724 B2 | 9/2009 | Purcell | |
| D607,919 S | 1/2010 | Williams | |
| D630,241 S | 1/2011 | Campbell | |
| D634,354 S | 3/2011 | Schwartz | |
| D640,733 S | 6/2011 | Ho | |
| D642,211 S | 7/2011 | Bilton | |
| D658,875 S | 5/2012 | Xiang | |
| D666,287 S | 8/2012 | Quinlan | |
| D667,484 S | 9/2012 | Anders | |
| D667,749 S | 9/2012 | Case | |
| D669,115 S | 10/2012 | Kalbach | |
| D672,384 S | 12/2012 | Brauner | |
| D677,189 S | 3/2013 | Kalbach | |
| 8,523,350 B2 | 9/2013 | Krisik et al. | |
| 8,590,539 B2 | 11/2013 | Froissard | |
| 8,671,949 B2 | 3/2014 | Oshima | |
| D705,421 S | 5/2014 | Eisenmenger | |
| D723,264 S | 3/2015 | Akana | |
| D730,315 S | 5/2015 | Stevinson | |
| D731,781 S | 6/2015 | Behar | |
| 9,101,795 B2 | 8/2015 | Anderson | |
| 9,167,330 B1 | 10/2015 | Shattuck | |
| D743,691 S | 11/2015 | Romano | |
| D767,665 S | 9/2016 | McSwain | |
| D771,010 S | 11/2016 | Louis | |
| D774,591 S | 12/2016 | Businger | |
| D781,570 S | 3/2017 | Andersen | |
| 2003/0223032 A1 | 12/2003 | Gagnon | |
| 2006/0196900 A1 | 9/2006 | Sasick | |
| 2007/0080186 A1 | 4/2007 | deLeon | |
| 2007/0081324 A1 | 4/2007 | Schrimmer | |
| 2007/0229296 A1 | 10/2007 | Kohrman | |
| 2007/0242214 A1 | 10/2007 | Carter | |
| 2008/0047996 A1 | 2/2008 | Blouin | |
| 2009/0165189 A1 | 7/2009 | Purcell | |
| 2010/0133307 A1 | 6/2010 | Martin | |
| 2010/0165286 A1 | 7/2010 | Martin | |
| 2010/0206925 A1 | 8/2010 | Fielding | |
| 2010/0302501 A1 | 12/2010 | Hansen | |
| 2013/0250230 A1 | 9/2013 | Huynh | |
| 2016/0183668 A1 | 6/2016 | Grossman | |
| 2016/0286943 A1 | 10/2016 | Andersen | |

OTHER PUBLICATIONS

US-Army-Military-Shop.DE, US Army Ear Plug Holder/Ear Plug Case, 2007-2009.

\* cited by examiner

LANYARD WITH INTEGRATED EAR PLUGS AND RETRACTABLE SHEATH

PRIORITY

The present application is a continuation of U.S. Ser. No. 14/677,861, filed Apr. 2, 2015, which is herein incorporated by reference in its entirety.

THE FIELD OF THE INVENTION

The present invention relates to safety devices. More specifically, the present invention relates to a lanyard with integrated ear plugs.

BACKGROUND

Many people have jobs which require them to wear safety gear such as safety glasses and ear plugs while working. It is important to ensure that the safety gear is properly utilized and properly managed to provide for the safety of the worker and, in many instances, to prevent problems with the items the person is working on.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention. The drawings are drawn to scale to allow for better understanding of the structures and components thereof.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Figure 1:
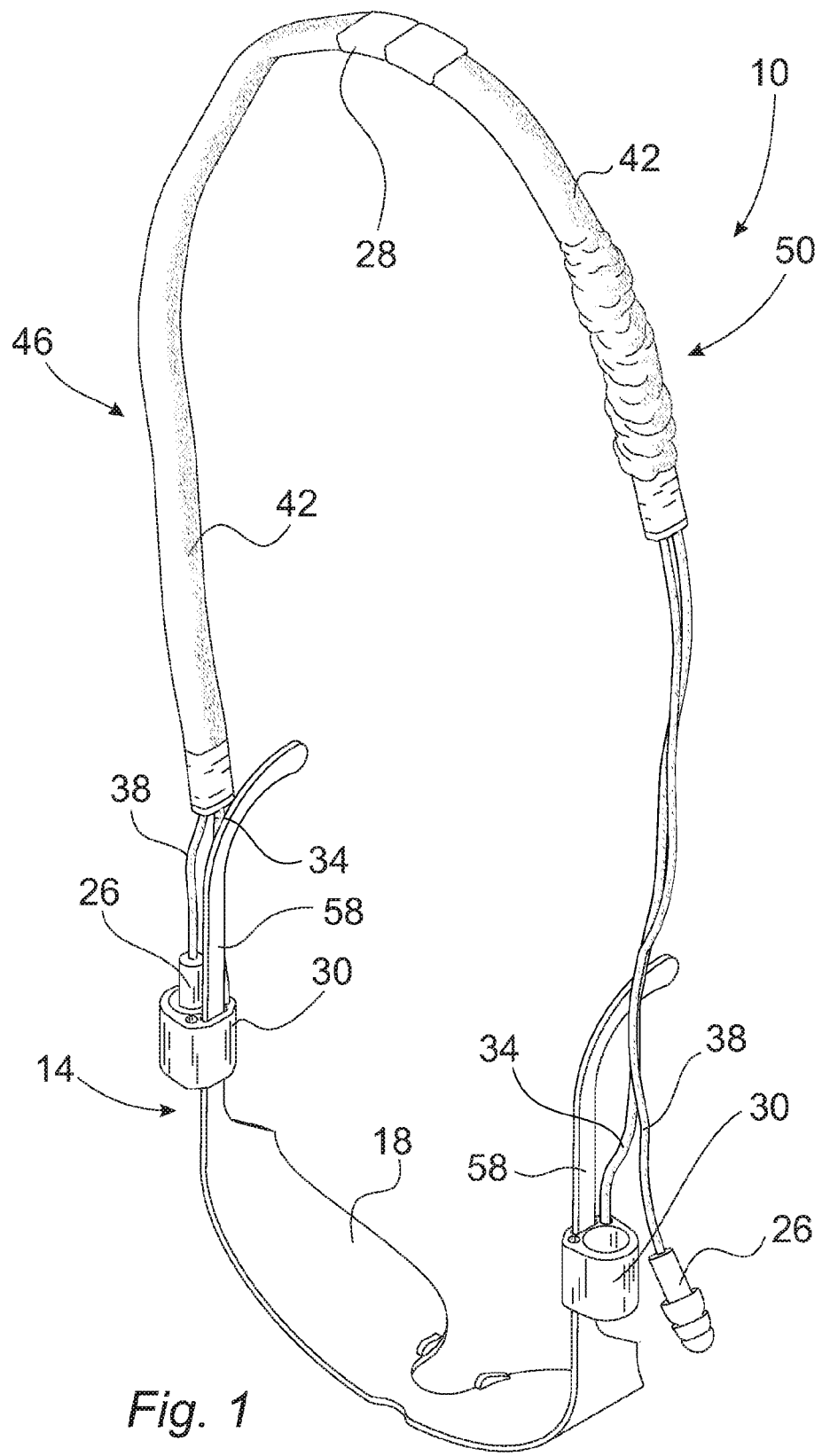
FIG. 1 shows a drawing of a lanyard.
Figure 2:
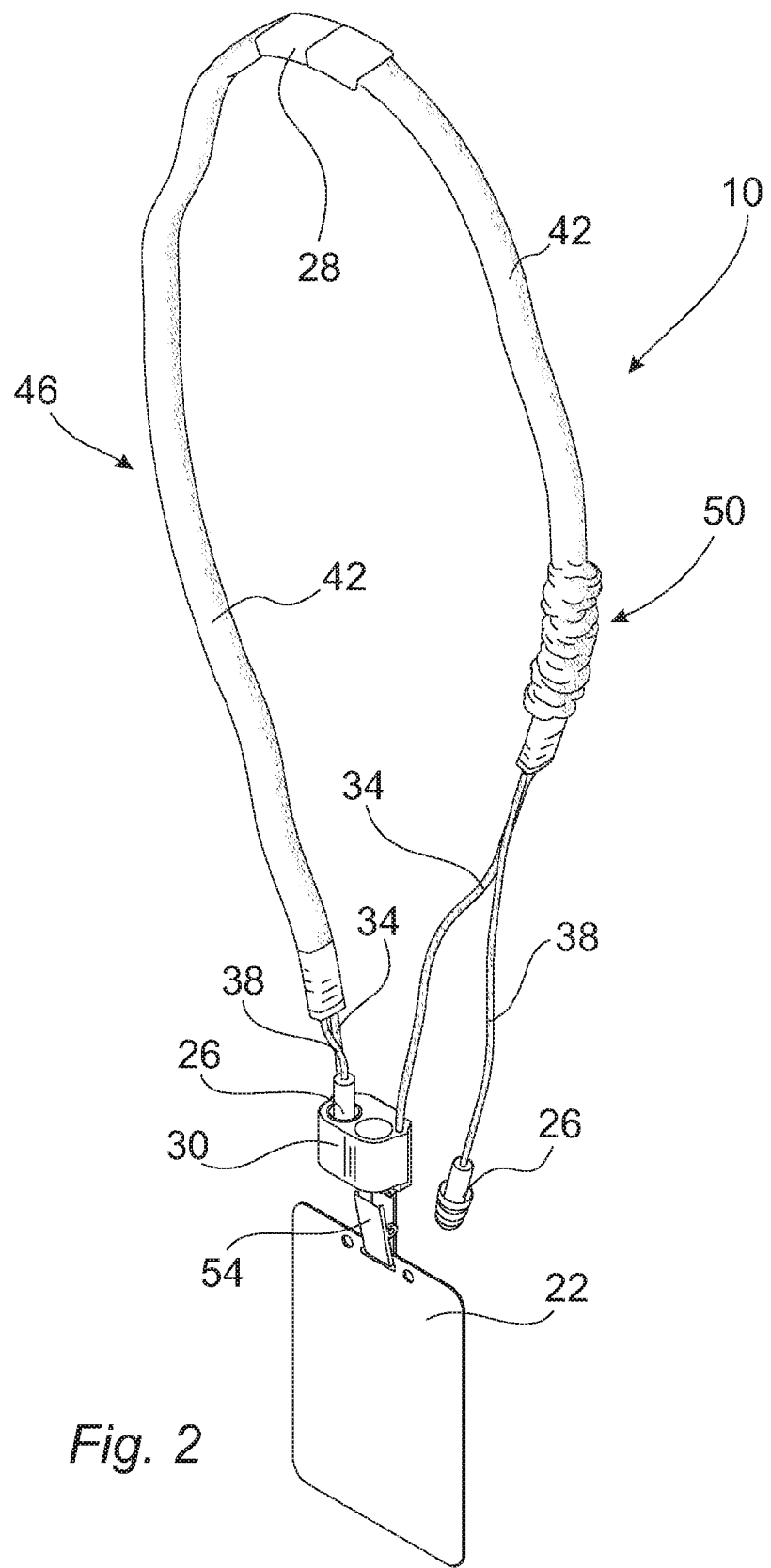
FIG. 2 shows a drawing of a lanyard.

Turning now to FIGS. 1 and 2, drawings of a lanyard with integrated ear plugs are shown. FIG. 1 shows a lanyard 10 attached to a pair of safety glasses. FIG. 2 shows a lanyard attached to an ID badge. The lanyard 10 carries a user's personal item 14 such as safety glasses 18 (FIG. 1) or an ID badge 22 (FIG. 2) and also provides integrated ear plugs 26 which may be extended or retracted from the lanyard as desired. The lanyard 10 retains the ear plugs and keeps them closely connected to the lanyard. This prevents loss of the earplugs 26 and keeps the earplugs clean and accessible to a user; encouraging use of the earplugs. The lanyard 10 is sized and constructed to allow a person to wear the lanyard around their neck. The lanyard 10 may include a clip 28 or other connector which separates the lanyard into two parts and allows the lanyard to be more easily placed around the user's neck. During use of the lanyard 10, earplugs 26 are kept within easy reach.

The earplugs 26 may be placed into a receiver 30 for storage while they are not in use and removed from the receiver when needed. The receiver 30 may also connect a lanyard cord 34 to a personal item 14. The lanyard may include a lanyard cord 34 which is attached to a person item 14 that is secured to the lanyard, an earplug cord 38 that is secured to the earplugs 26, and a retractable sheath 42 which selectively covers the lanyard cord 34 and the earplug cord 38. The lanyard includes a length of both the lanyard cord 34 and earplug cord 38 and the retractable sheath is disposable to cover a length of both the lanyard cord 34 and earplug cord 38. The lanyard cord 34 and earplug cord 38 are a flexible cord such as a nylon cord. The retractable sheath is a flexible tubular sheath such as a woven, braided, or knit cloth tube.

The retractable sheath 42 is tubular in nature and the lanyard cord 34 and earplug cord 38 extend into the retractable sheath 42. The retractable sheath is movable between an extended position (generally indicated at 46) and a retracted position (generally indicated at 50). In the extended position 46, the retractable sheath 42 covers a majority of the lanyard cord 34 and the earplug cord 38. A small amount of the lanyard cord 34 and earplug cord 38 extend from the retractable sheath 42 to allow the lanyard cord 34 and earplug cord 38 to attach to the receiver 30 or personal item 14 and the earplug 26 respectively.

In the retracted position 50, the retractable sheath 42 allows a significant length of the lanyard cord 34 and earplug cord 38 to extend from the end of the retractable sheath 42. As the retractable sheath 42 surrounds the lanyard cord 34 and earplug cord 38, the retractable sheath 42 is slid along the lanyard cord 34 and earplug cord 38 away from the personal item 14 and earplug 26. The retractable sheath 42 will typically bunch up and become shorter as it is retracted and the lanyard cord 34 and earplug cord 38 are exposed from the end thereof. Retracting the retractable sheath 42 as shown at 50 exposes a greater length of lanyard cord 34 and earplug cord 38 and thereby allows a user to place the earplugs in their ear more easily. This is particularly true where the lanyard is attached to an ID badge 22. Often it is desirable to allow approximately 10 inches of lanyard cord 34 and earplug cord 38 to be exposed by retracting an end of the retractable sheath 42. The lanyard 10 may typically be about 40 inches in length measured from one earplug 26 to the other earplug 26 or measured from one end of the lanyard cord 34 to the other end of the lanyard cord. It will be appreciated that, in use, a user will typically retract both sides of the retractable sheath 42 to allow for more easy use of the earplugs, but that the design allows for significant flexibility in how a user utilizes the lanyard 10.

In one example, the lanyard 10 does not include a clip 28 and may be continuous across the center portion of the lanyard typically placed around the user's neck. The retractable sheath 42, the lanyard cord 34 and the earplug cord 38 may extend continuously around the center portion of the lanyard (and around the neck of a user who is wearing the lanyard 10). In this example, the retractable sheath 42 may be a single piece of tube material. The lanyard cord 34 may be a single piece of cord. Both ends of the lanyard cord 34 may be attached to the personal item 14, such as via one or more earplug receivers 30.

In another example, the lanyard includes a connector 28 such as a snap, hook and loop fastener, or clip which allows the lanyard 10 to be separated into two pieces. This allows a user to more easily place the lanyard 10 around their neck or remove the lanyard from their neck. As an example, this may be desirable where the lanyard 10 is shorter to keep any loops of lanyard around the user's body to a minimum. In situations where a person works around moving parts (e.g. a machine shop, around engines, etc.) this may greatly reduce the risk that the lanyard catches on a moving part. In such a situation, the overall length of the lanyard 10 may be about 30 inches. In this example, the lanyard cord 34, earplug cord 38, and retractable sheath 42 are separated by the connector 28. There are thus two pieces of lanyard cord 34, earplug cord 38, and retractable sheath 42 connecting the two ends of the connector 28 to the appropriate earplugs 26, personal item 14, or receiver 30.

As is shown in FIG. 1, the lanyard 10 may include two receivers 30. Each receiver 30 may attach to a temple 58 of the glasses 18. Each receiver 30 may attach to the glasses 18 and to an end of the lanyard cord 34, and may have an opening to receive an earplug 26. As is shown in FIG. 2, the lanyard 10 may include a single receiver 30. The receiver 30 may attach to a card 22 such as an ID badge or access card. Typically, the receiver 30 attaches to a card holder 54 such as a clip or retaining loop and the card holder is attached to the card 22. The receiver 30 may attach to two ends of the lanyard cord 34 and may have two openings which receive earplugs 26.

The receiver 30 may be formed from a variety of materials. In one example, the receiver 30 may be formed from an elastomeric material. The receiver may be a molded silicone or rubber. A receiver 30 formed from a soft material may allow the receiver to be attached to different types of glasses 18, for example. Additionally, a soft receiver 30 may better accommodate a harder earplug 26. In another example, the receiver 30 may also be formed from a hard material such as a plastic. This may be advantageous where the receiver is made for a specific pair of glasses 18 or a specific card holder 54 and where the earplugs 26 are soft and do not need a compliant receiver 30.

Figure 3:
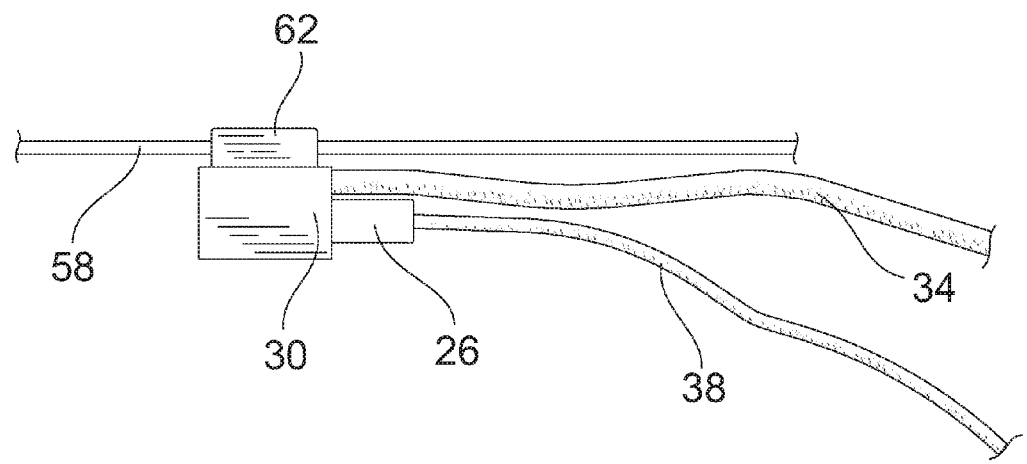
FIG. 3 shows a drawing of the lanyard receiver.
Figure 4:
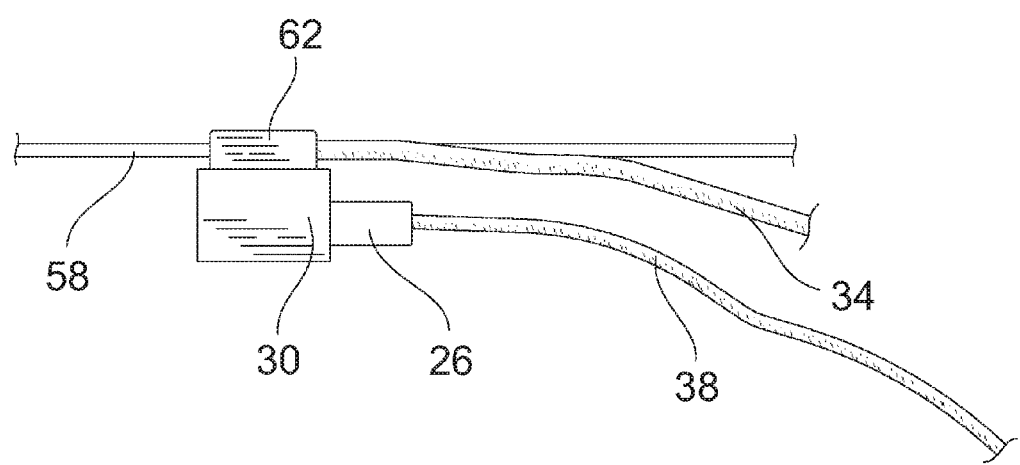
FIG. 4 shows a drawing of the lanyard receiver.

Referring now to FIG. 3, a top view of a portion of a glasses temple 58 as illustrated in FIG. 1 is shown. The receiver 30 has been formed from two materials/components. The receiver may include a clamp 62 attached to a receiver body 30. The clamp 62 may attach to the temple 58 and the receiver body 30 may receive the earplug 26 and lanyard cord 34. Alternately, FIG. 4 shows a configuration where a receiver 30 includes a clamp 62 attached to glasses temples 58 and which receives the lanyard cord 34. The clamp 62 is attached to a receiver body 30 which receives the earplugs 26. This allows different materials to be combined to best accommodate a particular glasses 18 and earplug 26.

Figure 5:
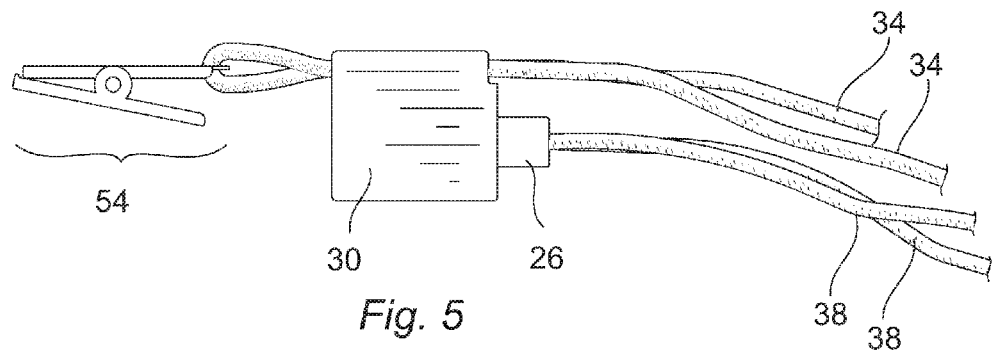
FIG. 5 shows a drawing of the lanyard receiver.
Figure 6A:
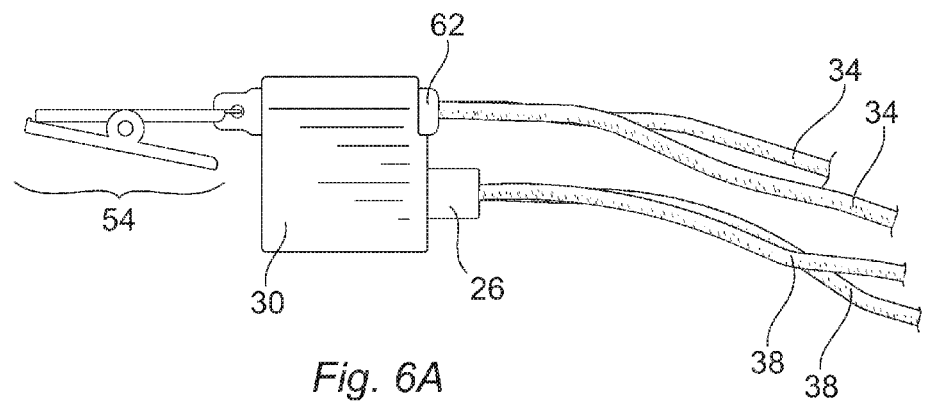
FIG. 6A shows a drawing of the lanyard receiver.
Figure 6B:
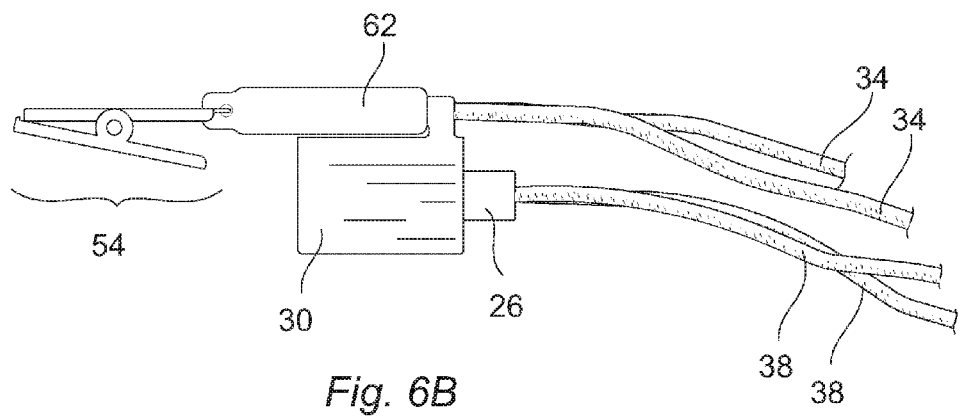
FIG. 6B shows a drawing of the lanyard receiver.

Referring now to FIG. 5, a side view of a receiver 30 for a card lanyard 10 is shown. The receiver 30 may be attached to a card holder 54 and be attached to the ends of the lanyard cord 34 and may hold earplugs 26. Alternately, FIG. 6A shows a configuration where the receiver 30 includes a clamp portion 62 which is attached to a card holder 54 (e.g. a clip). The clamp 62 may also be attached to the ends of the lanyard cord 34. The clamp portion 62 is also attached to the receiver body 30 which holds earplugs 26. For example, the clamp portion 62 may be inserted through a channel formed in the receiver body 30. Where an elastic receiver body is used, the clamp may be pushed into a hole through the receiver body which is slightly smaller than the clamp 62 and thereby holds the clamp securely. FIG. 6B shows a configuration which includes a clamp 62 that is attached to a card holder 54 such as a clip, swivel, etc. The clamp 62 attaches to the receiver body 30 by clamping over a tongue which extends from the receiver body 30.

Figure 7A:
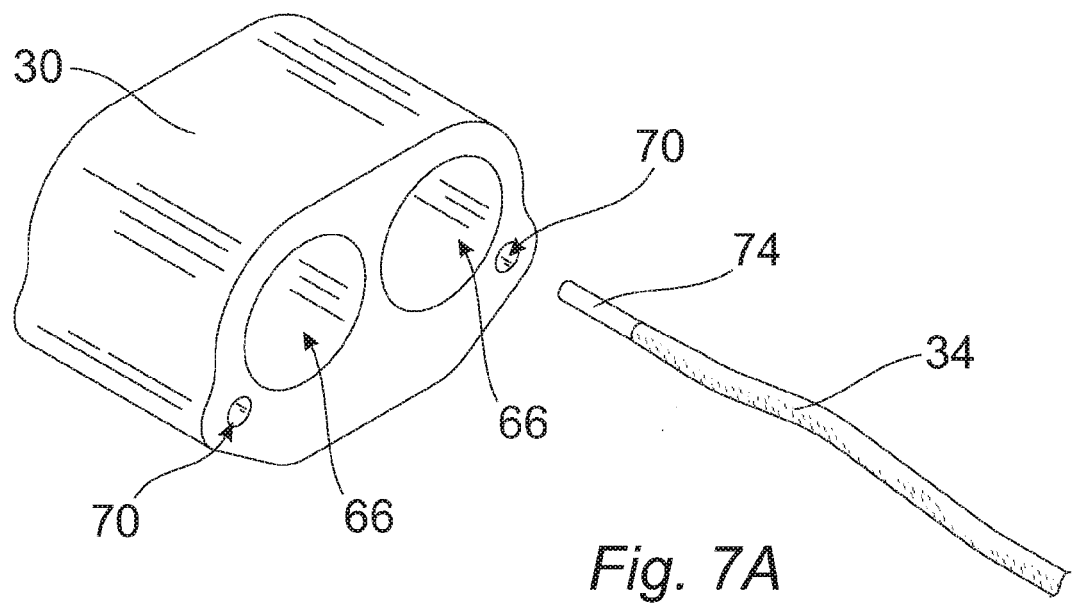
FIG. 7A shows a drawing of the lanyard receiver.

Referring now to FIG. 7A, a perspective view of a receiver body 30 are shown to better illustrate some of the structures of the receiver body. As discussed, the receiver body 30 may be formed from an elastic material such as molded silicone or rubber. The receiver body 30 may include receptacles 66 which receive earplugs 26. For many earplugs, the receptacles 66 may be round holes extending a distance into the receiver 30. The examples show earplugs 26 which have round cups molded around a center stem. These earplugs are common and fit well into a round receptacle 66. The receptacles 66 will typically have distal ends which are largely closed so that the earplug is prevented from insertion completely through the receiver body 30. The distal ends of the earplug receptacles 66 may have small holes which extend through the receiver body to prevent air pressure differentials which make it more difficult to insert or remove an earplug 26.

Typically, the earplugs 26 are an interference fit in the receptacles 66; requiring the earplugs 26, receptacles 66, or both to deform somewhat when the earplug 26 is inserted into the receptacle 66. The receiver 30 may also be formed with holes 70 for attachment to the lanyard cord 34. In one example, the ends of the lanyard cord 34 may be covered with an aglet 74 and the aglet may be an interference fit into a hole 70 of an elastomeric receiver 30. If the aglet 74 is larger than the hole 70, it may be held securely in the receiver 30 after insertion. The cord 34 may be formed with an aglet 74 which leaves a pronounced shoulder on the proximal end of the aglet where the aglet terminates over the cord 34. This shoulder may be disposed into the hole 70 and a hole 70 in an elastomeric receiver body 30 which is smaller in diameter than the aglet will contract around the cord and grip the shoulder and prevent easy removal of the aglet from the hole. The lanyard cord 34 may also be glued or molded into the receiver body 30 for certain constructions.

Figure 7B:
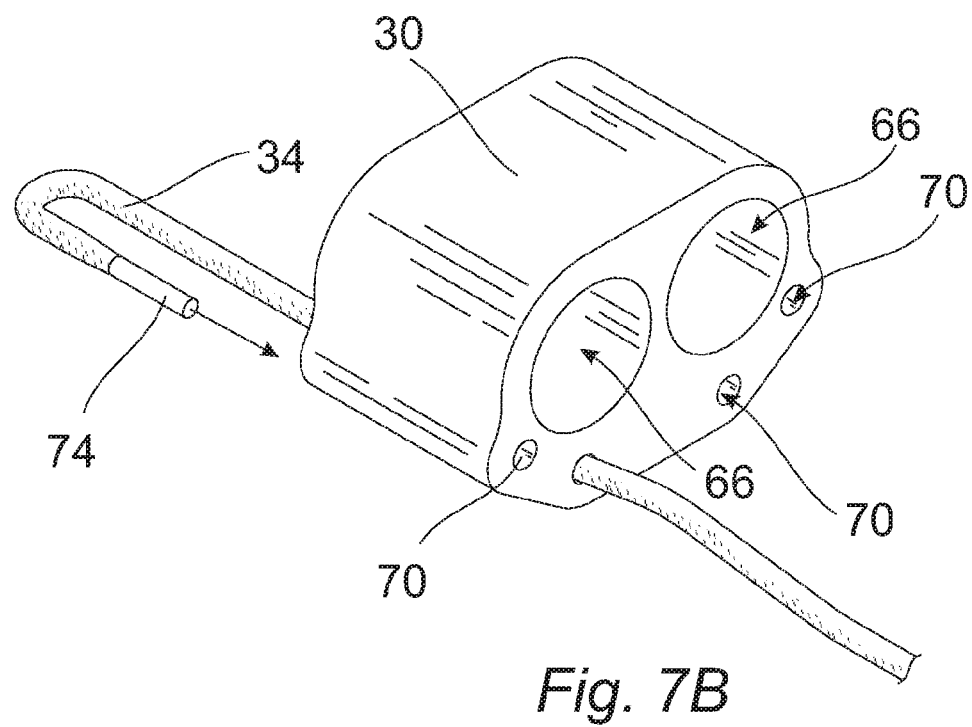
FIG. 7B shows a drawing of the lanyard receiver.

FIG. 7B shows a receiver body 30 which is similar to the receiver body shown in FIG. 7A, but which includes additional holes 70. The additional holes 70 may be used to more securely attach a cord 34 to the receiver body 30. As is illustrated, a cord 34 with an aglet 74 on the end of the cord may be used. The aglet 74 and the end of the cord 34 may be passed through a first hole 70, the aglet turned about 180 degrees, and the aglet then passed into a second hole 70 so that the cord 34 loops back as shown. The aglet 74 is typically disposed in a hole 70 so that the aglet is roughly centered within the hole 70 and the receiver body 30 extends both in front of and behind the aglet 74. Any excess loop of the cord 34 may be retracted through the first hole 70. This secures the cord 34 to the receiver body in a simple manner which is unlikely to come apart even when the lanyard is subjected to considerable strain or abuse.

Figure 8:
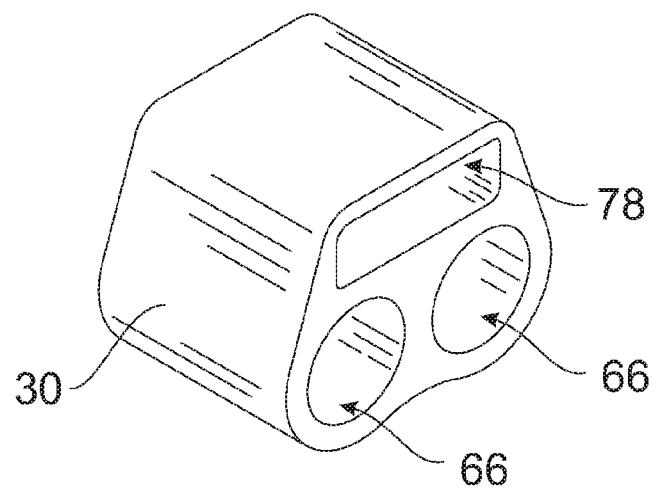
FIG. 8 shows a drawing of the lanyard receiver.

FIG. 8 shows a receiver body 30 which includes a larger hole 78 to receive a clamp 62 or card holder 54 as illustrated in FIGS. 5 and 6A. The clamp fits insides of the hole 78, often extending through the hole. An elastic receiver body 30 may be formed with a hole 78 which is smaller than the clamp 62 so that the receiver body 30 grips the clamp 62 and prevents easy withdrawal of the clamp 62 from the hole 78. This allows for assembly of the lanyard without using adhesive. The clamp 62 may be formed with ridges extending circumferentially around the body of the clamp. These ridges may be gripped by a hole 78 which is slightly smaller than the clamp 62 and prevent easy withdrawal of the clamp 62 from the hole 78.

Figure 9A:
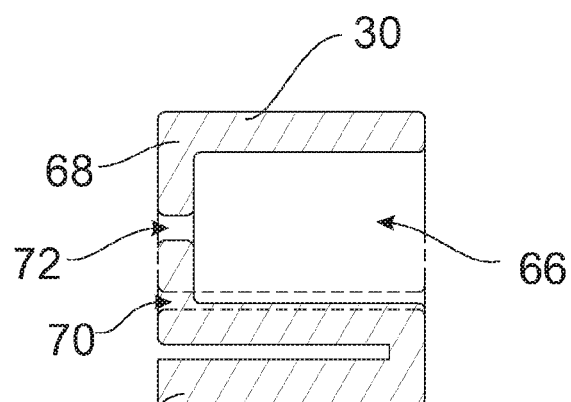
FIG. 9A shows a drawing of the lanyard receiver.
Figure 9B:
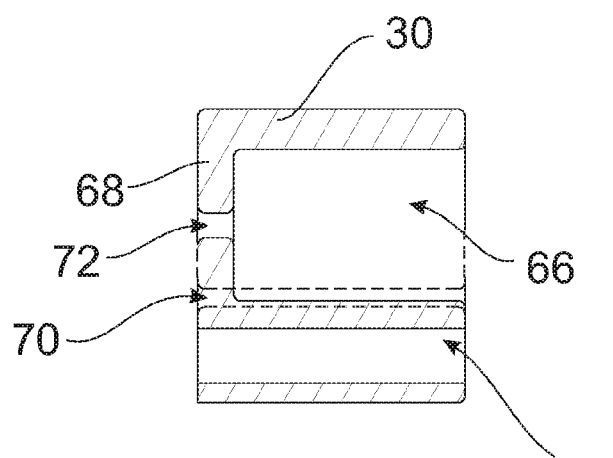
FIG. 9B shows a drawing of the lanyard receiver.
Figure 10:
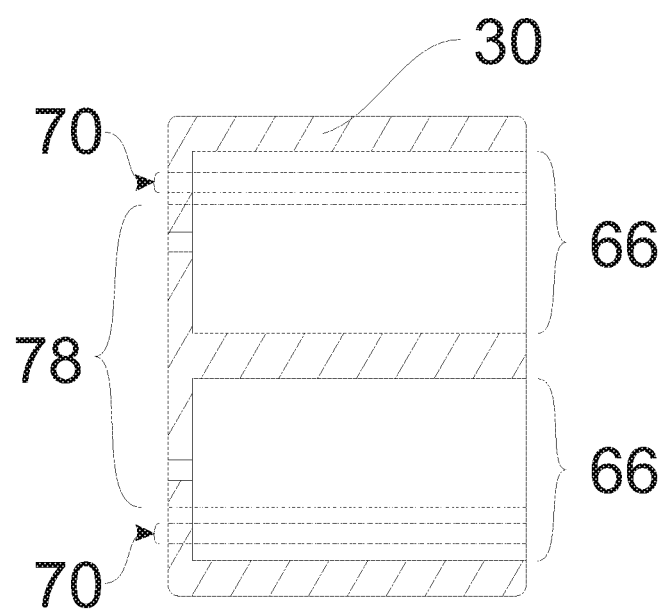
FIG. 10 shows a drawing of the lanyard receiver.

FIGS. 9A, 9B, and 10 show sectional views of example receiver bodies 30, illustrating the various openings formed therein. FIG. 9A shows a sectional view of a receiver body 30 as shown in FIG. 8B. As discussed, the receiver body includes earplug receptacles 66 which receive and store earplugs 26. These figures illustrate how the receptacles 66 may be open proximally and have a distal wall 68 which substantially closes the distal end of the receptacle 66. A hole 72 may be formed in the distal wall to eliminate air pressure differentials as earplugs are inserted into or removed from the receptacles 66. The receiver body 30 may also include one or more holes 70 for use as discussed herein. The receiver body 30 may be formed with a tongue 76. The tongue may extend from the receiver body 30 and may extend parallel to the receiver body 30. As discussed, a clamp 62 may be attached to the tongue 76 in order to attach the receiver body to an ID card clip 54 and lanyard cords 34.

FIG. 9B shows a sectional view of a receiver body 30 such as is shown in FIGS. 6A and 8. As discussed, the receiver body 30 may include earplug receptacles 66 with corresponding distal walls 68 and pressure vent holes 72. A larger clamp receiving hole 78 may be formed in the receiver body 30 to receive the card holder 54 for a card holding lanyard 10 or to receive a clamp 62 as has been discussed. The hole 78 may be formed in an end of the receiver body 30 such as the distal end of the receiver body. Alternatively, the hole 78 may be formed through the receiver body. As mentioned, the card holder 54 or clamp 62 may be inserted into an elastomeric receiver body 30 and held there by friction or may also be glued or co-molded into the receiver body 30. FIG. 10 shows a sectional top/bottom view of the receiver body 30 and illustrates earplug receptacles 66 may be positioned side by side and how additional holes 70, 78 may be positioned above or below the earplug receptacles 66.

Figure 11A:
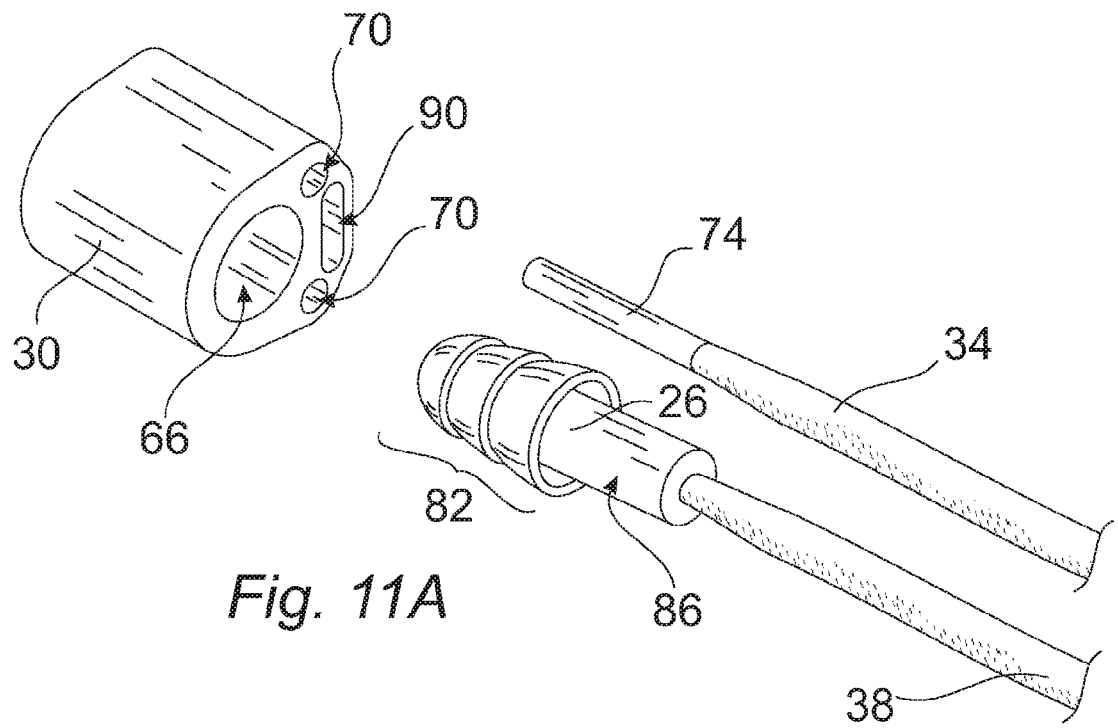
FIG. 11A shows a drawing of the lanyard receiver and earplug.
Figure 11B:
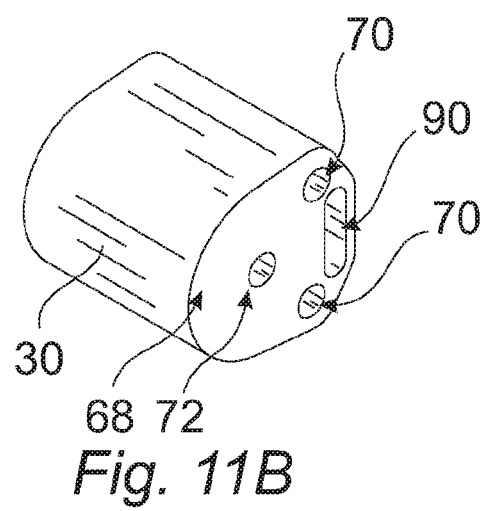
FIG. 11B shows a drawing of the lanyard receiver.

Referring now to FIGS. 11A and 11B, perspective views of a receiver 30 for a lanyard 10 which is used holds glasses 18 such as safety glasses is shown. FIG. 11A shows the receiver body 30, cord 34, earplug 26, and earplug cord 38. FIG. 11B shows a perspective view of the opposite end of the receiver body 30. The receiver body 30 may include a receptacle 66 which receives an earplug 26. As discussed, receptacle may be generally closed by a distal wall. A vent hole 72 may be provided in the distal wall to facilitate placement of and earplug 26 in the receptacle 66. The receiver body 30 may also include one or more holes 70 which are used to secure an end of the lanyard cord 34. As discussed, the lanyard cord may be attached with an aglet 74 which is pressed into the hole 70, or which is passed through one hole 70, turned around, and pressed back into a second hole 70. The earplugs 26 may be formed with an earplug body 82 and a stem 86. The stem 86 may have a hole along its longitudinal axis and open to the back end of the stem and the end of the earplug cord 38 may be attached into the earplug stem hole. The earplug cord 38 may be terminated with an aglet which is pressed into the hole in the earplug stem 86. The body 82 of the earplug may be formed with soft cups as shown. Other earplug shapes may be used with the receiver body 30 since the receiver body may be formed from a soft material such as silicone. The receiver body 30 may also include a glasses mounting hole 90 which extends through the receiver body. The hole 90 may have an elongate cross-section such as the oval cross section shown so that the hole 90 is shaped to receive the temple 58 of the glasses 18. A user may install the lanyard onto a desired pair of glasses by sliding the hole 90 over the temple of the glasses.

Figure 12A:
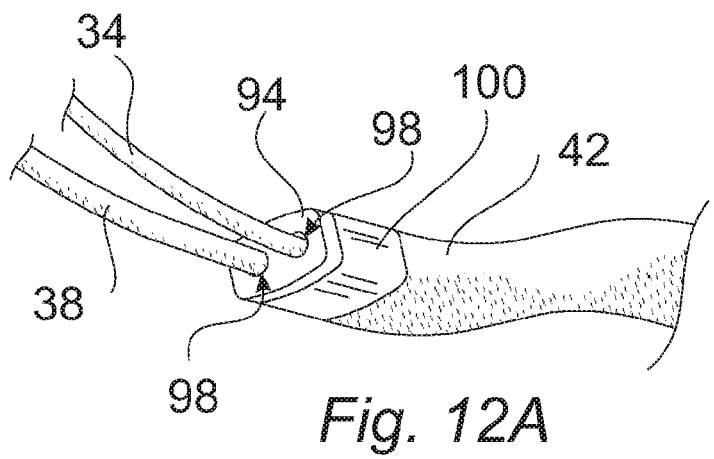
FIG. 12A shows a drawing of the lanyard cord separator and sheath.
Figure 12B:
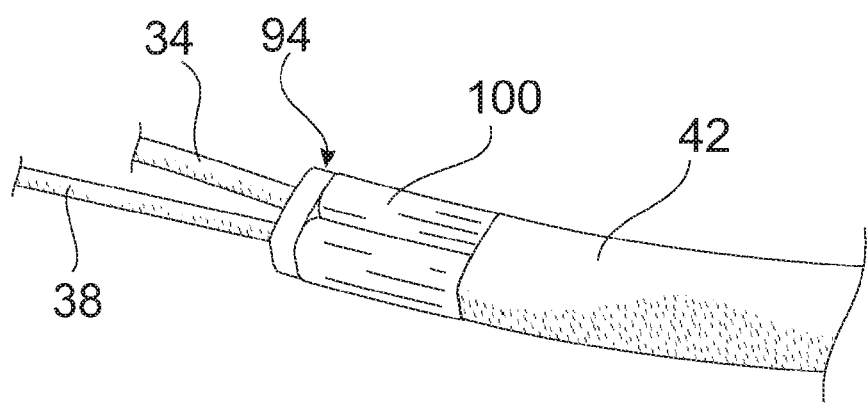
FIG. 12B shows a drawing of the lanyard cord separator and sheath.
Figure 12C:
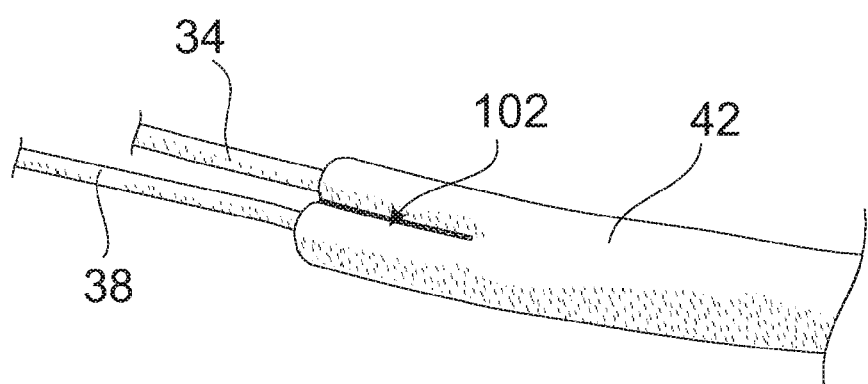
FIG. 12C shows a drawing of the lanyard cord separator and sheath.

Referring now to FIGS. 12A through 12C, perspective views of an end of the retractable sheath 42 are shown. The retractable sheath 42 may be formed with a cord separator 94. The cord separator 94 may be round or oval in cross-sectional shape and be sized to fit inside the retractable sheath 42. The cord separator 94 is often about two or three times longer than it is wide. Often, the cord separator is about 0.3 inches wide and about 0.8 inches long. The cord separator 94 is inserted into an end of the retractable sheath 42 and is secured to the end of the retractable sheath. The cord separator 94 has two holes 98 formed through its length. The lanyard cord 34 and earplug cord 38 pass through the holes 98 and into the lumen of the retractable sheath 42. The cord separator 94 keeps the lanyard cord 34 and earplug cord 38 from twisting within the retractable sheath 42 and thus promotes ease of use of the lanyard. The cord separator 94 may be a plastic piece and may be attached to the retractable sheath with a clamp 100 which extends around the end of the retractable sheath 42 and a portion of the cord separator 94. The clamp 100 may be heat shrink tube which may be adhesive lined. The clamp 100 may be a compressive band, ferrule clamp or the like.

FIG. 12B shows an end of the retractable sheath 42 which separates the cords 34, 38 with a clamp 100 such as a ferrule clamp. The ferrule clamp 100 may be attached around the end of the retractable sheath 42 as discussed. If desired, the ferrule clamp 100 may be used in combination with a cord separator 94 that is inserted into the retractable sheath 42 so that the retractable sheath is clamped between the cord separator 94 and the clamp 100. In some examples, a ferrule clamp may be used as a clamp 100 to separate the cords 34, 38 without anything else inserted into the retractable sheath 42. The ferrule clamp 100 may have ends which are crimped into a B shape as is shown. The ends of the ferrule clamp 100 separate the cords 34, 38 into opposite sides of the ferrule clamp 100 and keep the cords separated as discussed. FIG. 12C shows an end of the retractable sheath 42 which has been sewn 102 to separate the cords 34, 38.

Figure 13:
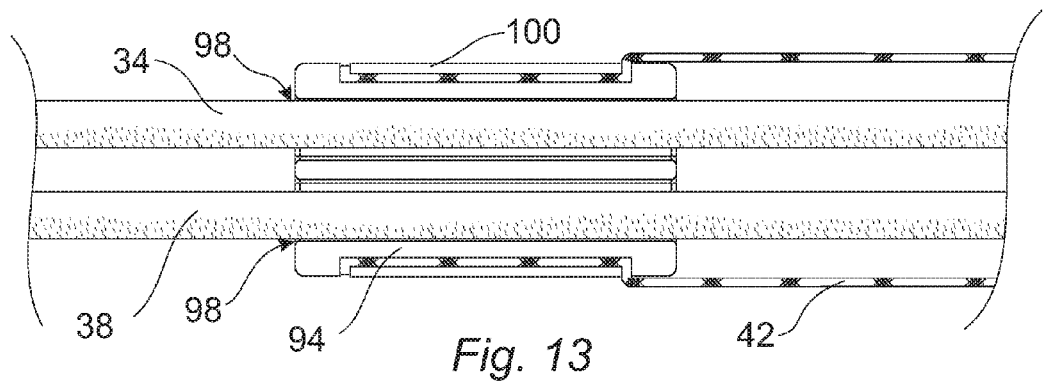
FIG. 13 shows a drawing of the lanyard cord separator and sheath.

Referring now to FIG. 13, a partial cross-sectional view of an end of the retractable sheath 42 is shown. The cord separator 94 and retractable sheath 42 are shown in cross-section. It can be seen how the holes 98 extend through the cord separator 94 and communicate with the lumen of the retractable sheath 42. This allows the lanyard cord 34 and earplug cord 38 to pass through the holes 98 and into the lumen of the retractable sheath 42. The retractable sheath 42 may be disposed over a part of the exterior of the cord separator 94 and be secured thereto by a clamp 100 such as a crimp ring, ferrule, shrink tubing, etc. In one example, a section of adhesive lined heat shrink tube may be shrunk over the cord separator 94 as a clamp 100 so that the heat shrink tube covers a portion of both the cord separator 94 and the retractable sheath 42 and secures them together. In use, a person may easily grasp the cord separator 94 and cords 34, 38 and slide the cord separator 94 along the lanyard cord 34 and earplug cord 38 to expose more of the cords. The user may also grasp the cord separator and pull on it to extend the retractable sheath 42 and cover the exposed lanyard cord 34 and earplug cord 38. The cord separator 94 keeps the lanyard cord 34 and earplug cord 38 from becoming twisted inside of the retractable sheath 42 and greatly simplifies the use of the lanyard 10. These examples discuss how the ends of the retractable sheath 42 may be terminated to separate the cords 34, 38 from each other as they enter the lumen of the retractable sheath 42. This keeps the cords 34, 38 from becoming twisted within the retractable sheath 42 and facilitates easy use of the lanyard 10.

Figure 14A:
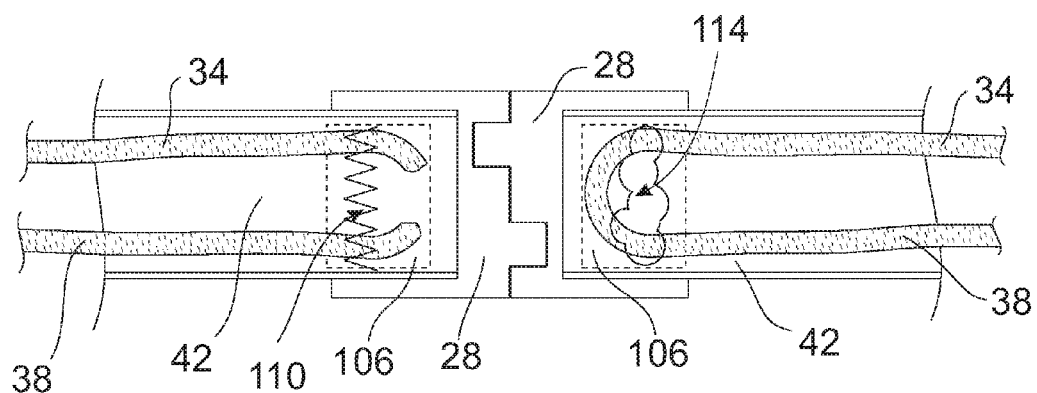
FIG. 14A shows a drawing of the lanyard connector.
Figure 14B:
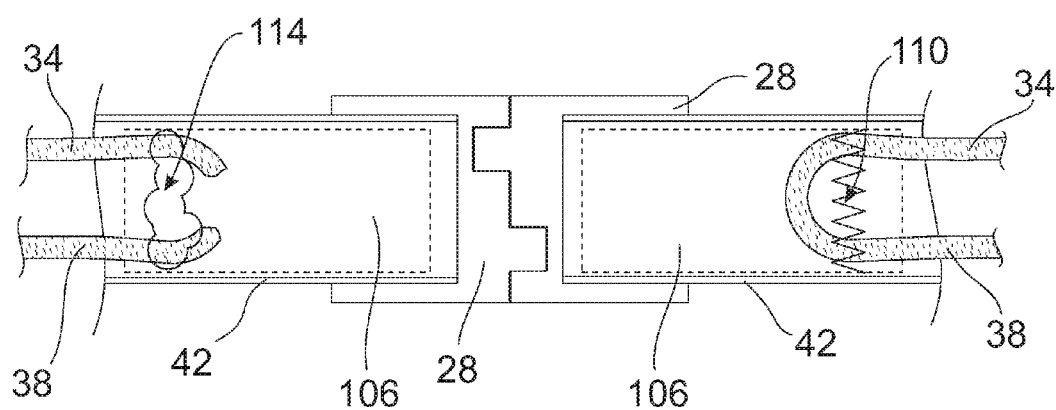
FIG. 14B shows a drawing of the lanyard connector.

Referring now to FIGS. 14A and 14B, schematic views of the connector 28 are shown. In one example, the connector may include male and female portions of a clip or quick release connector. The lanyard cord 34, earplug cord 38, and retractable sheath 42 may be terminated at the connector 28. Although not strictly necessary, extending the lanyard cord 34, earplug cord 38, and retractable sheath 42 into or adjacent to the connector 28 allows the user the greatest flexibility in positioning the retractable sheath and exposing the earplug cord 38 for use. The lanyard cord 34, earplug cord 38, and retractable sheath 42 may all be joined together at a joint which is near or inside of the connector 28. In one example, the joint may be formed by a piece of cloth or material 106 which encloses the cords 34, 38. The cords 34, 38 may be sewn 110 or glued 114 to the material 106. The retractable sheath 42 may also be attached to the cloth/fabric/material 106 used to form the joint and the material 106 may be placed inside of our outside of the retractable sheath. A joint formed with a piece of material 106 may be more easily attached to some connectors 28 as some connectors may not be designed to receive the bulk of the cords 34, 38. In these situations, it may be desirable to join the cords 34, 38 and/or the retractable sheath 42 with a piece of material 106 which is more easily and securely joined to the connector 28. In some situations, a joint may be formed by securing the cords 34, 38 within the retractable sheath 42 and then attaching the retractable sheath to the connector 28. For example, the cords 34, 38 may be inside of the retractable sheath 42 and all of these may be sewn through at a location to secure the cords 34, 38 to the retractable sheath.

Figure 15:
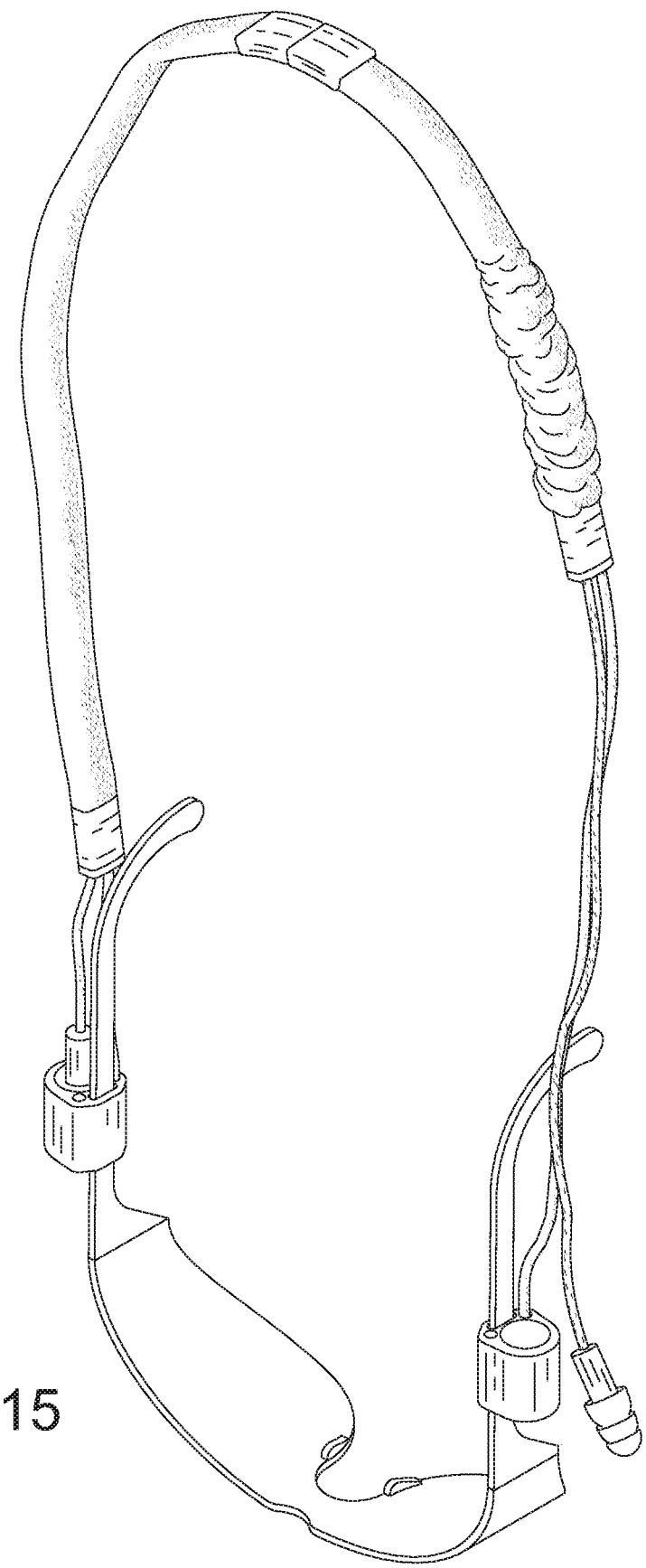
FIG. 15 shows a drawing of the lanyard.
Figure 16:
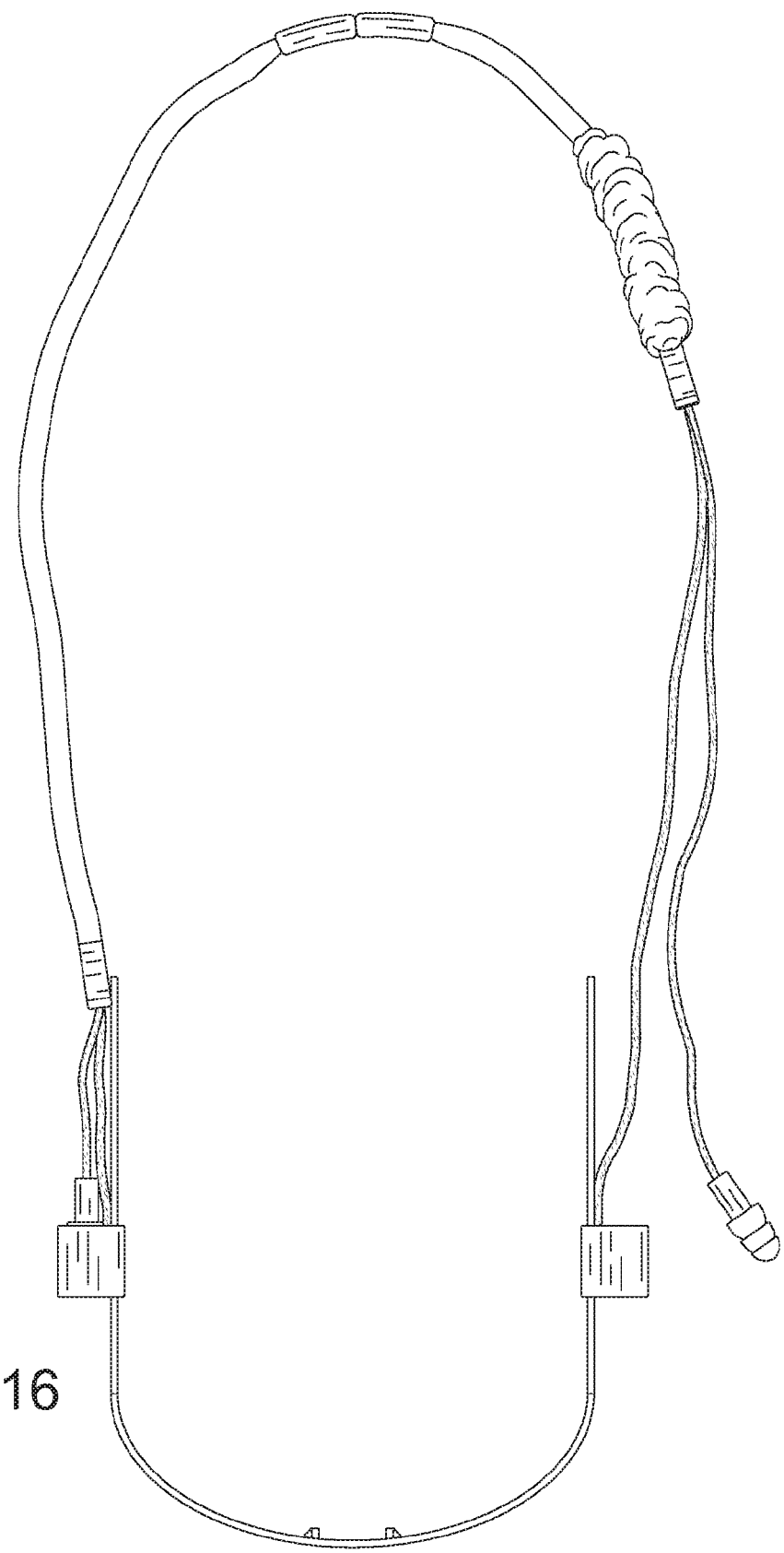
FIG. 16 shows a drawing of the lanyard.
Figure 17:
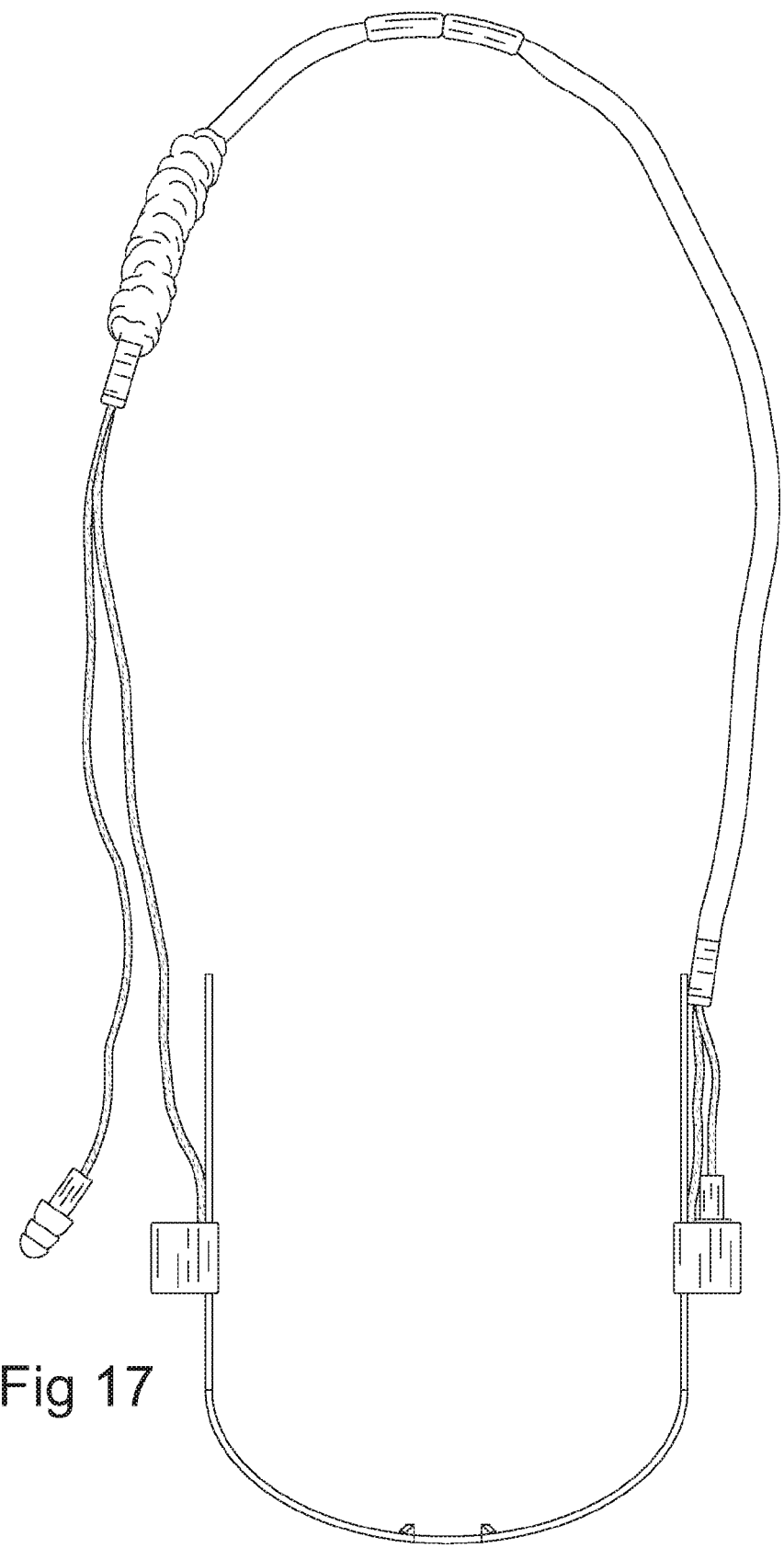
FIG. 17 shows a drawing of the lanyard.
Figure 18:
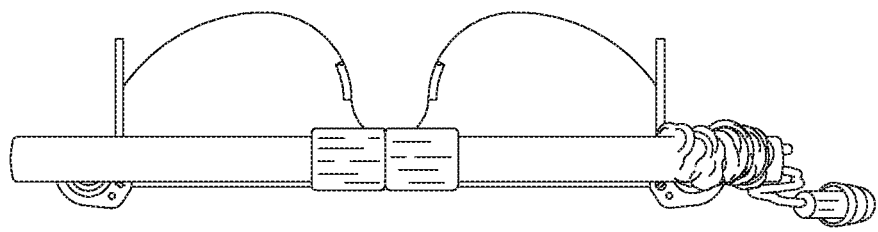
FIG. 18 shows a drawing of the lanyard.
Figure 19:
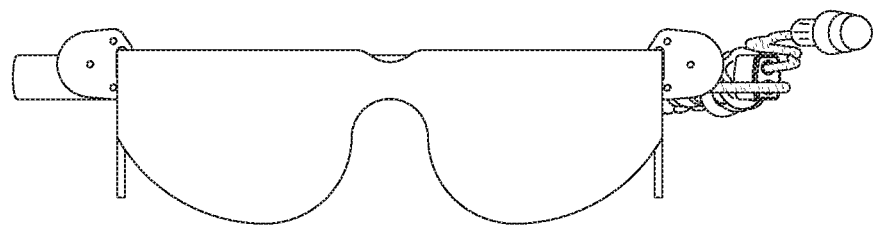
FIG. 19 shows a drawing of the lanyard.
Figure 20:
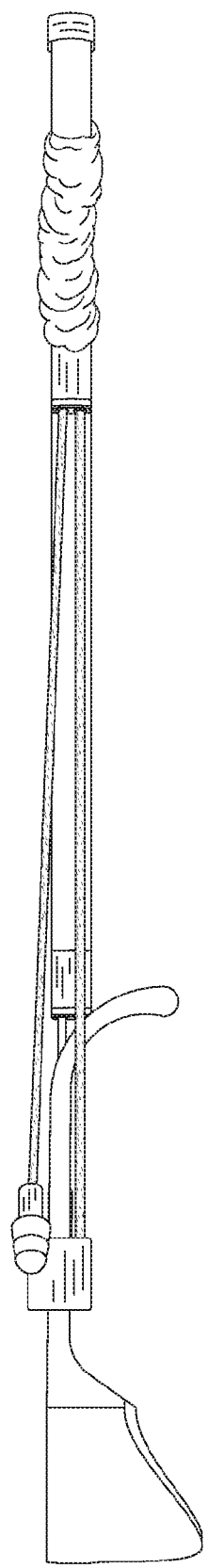
FIG. 20 shows a drawing of the lanyard.
Figure 21:
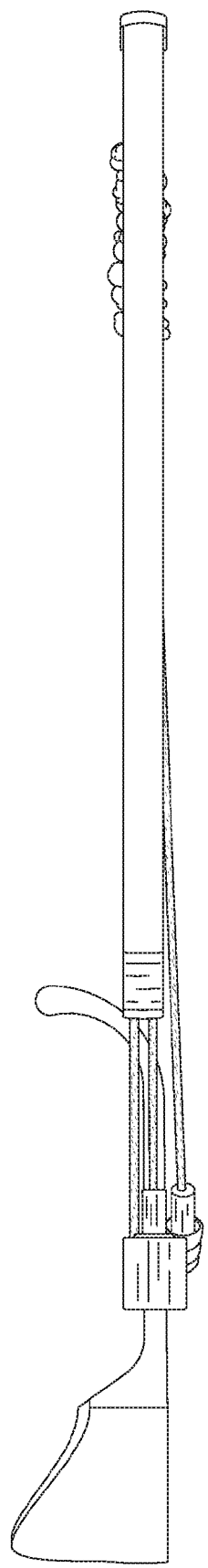
FIG. 21 shows a drawing of the lanyard.
Figure 22:
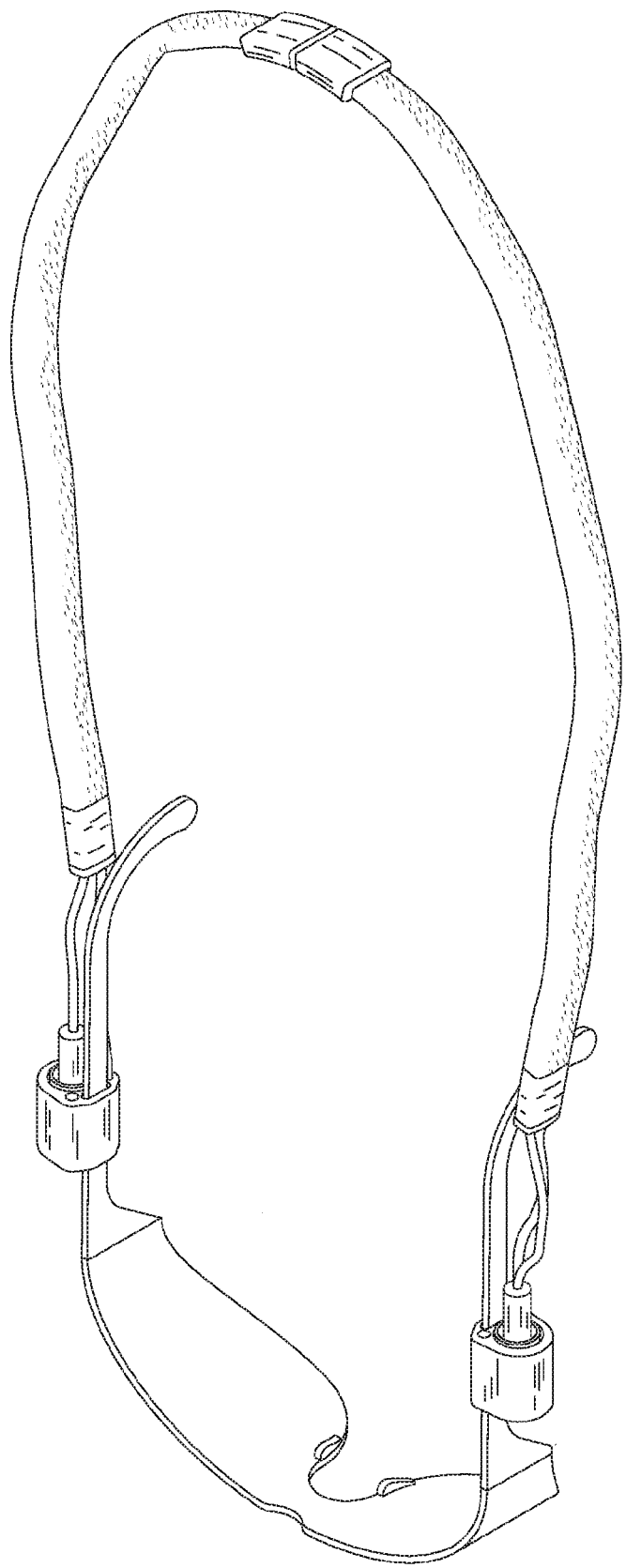
FIG. 22 shows a drawing of the lanyard.
Figure 23:
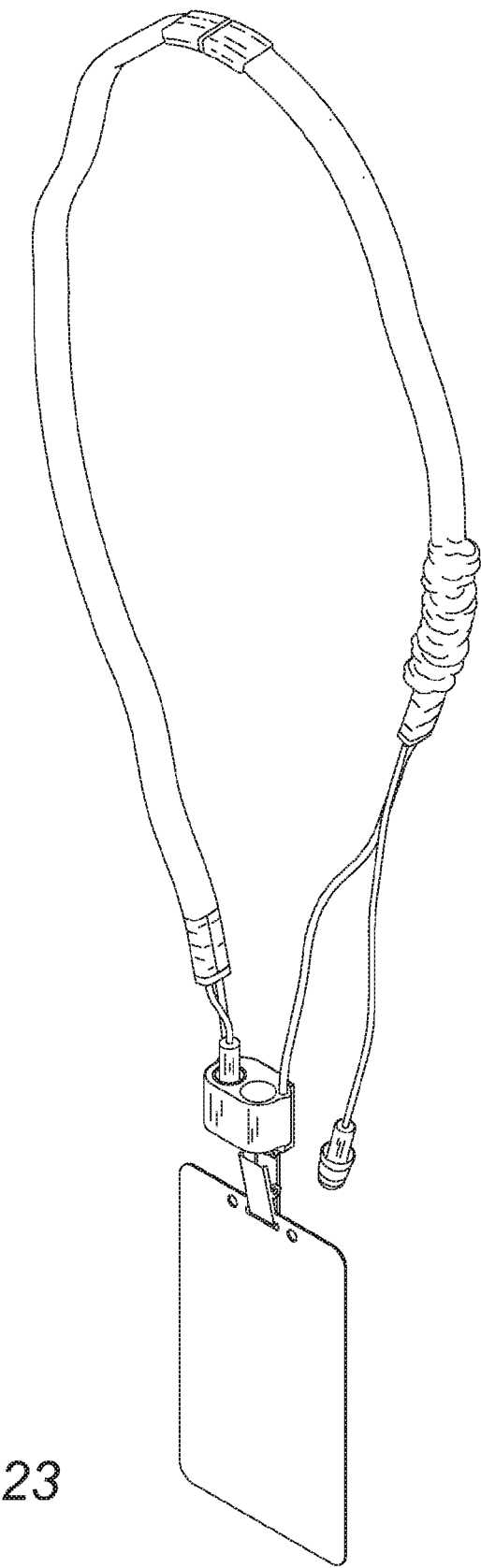
FIG. 23 shows a drawing of the lanyard.
Figure 24:
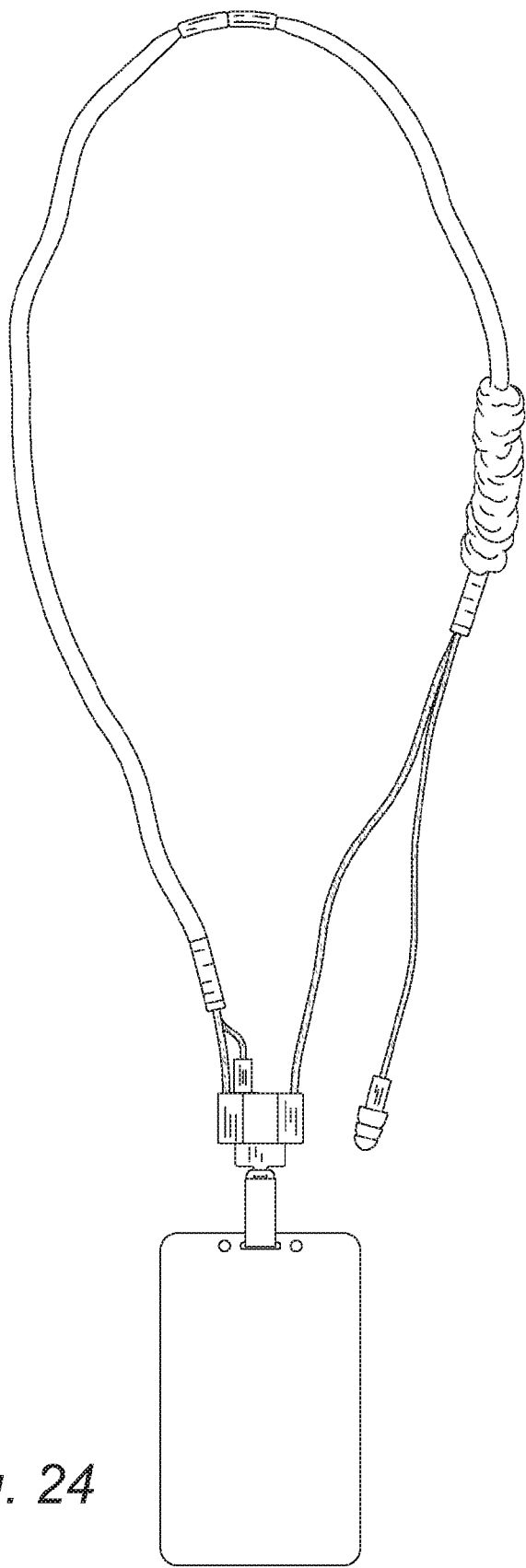
FIG. 24 shows a drawing of the lanyard.
Figure 25:
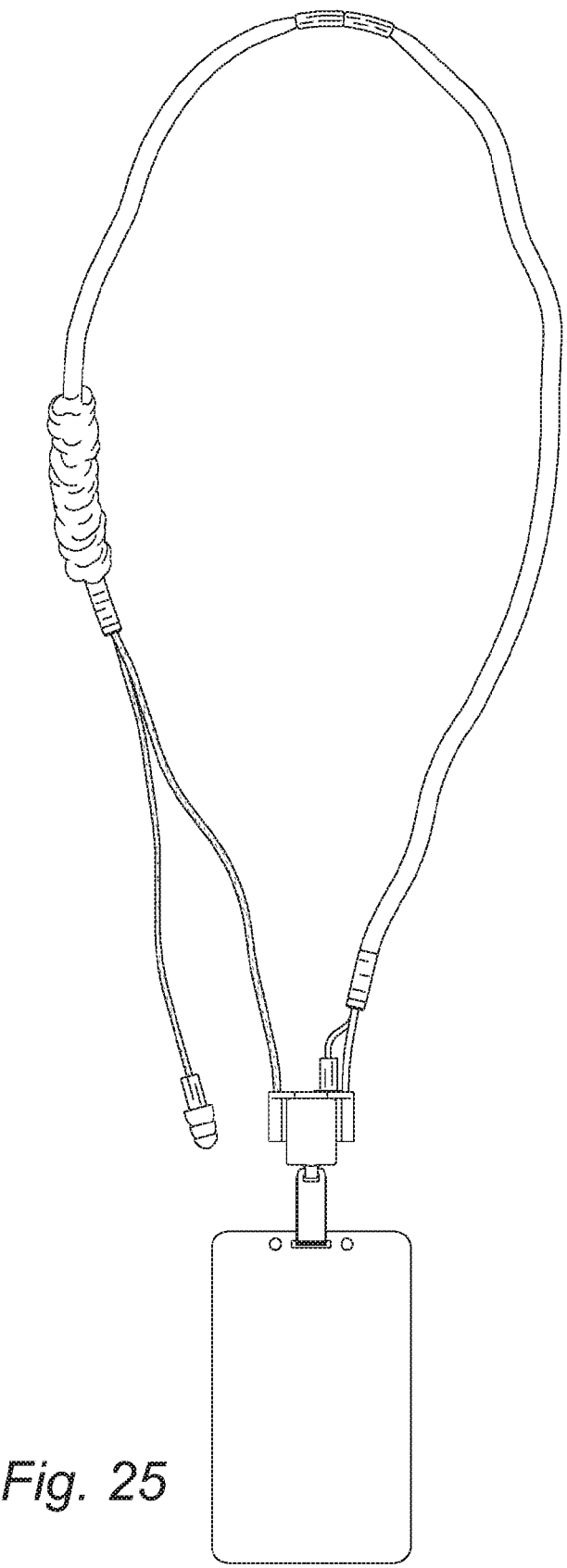
FIG. 25 shows a drawing of the lanyard.
Figure 26:
FIG. 26 shows a drawing of the lanyard.
Figure 27:
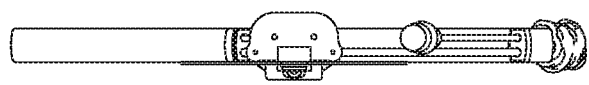
FIG. 27 shows a drawing of the lanyard.
Figure 28:
FIG. 28 shows a drawing of the lanyard.
Figure 29:
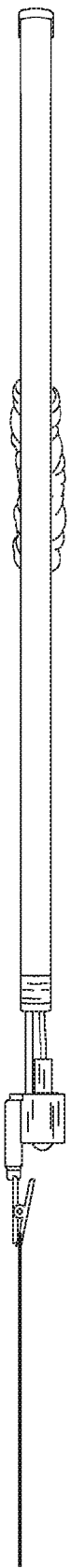
FIG. 29 shows a drawing of the lanyard.
Figure 30:
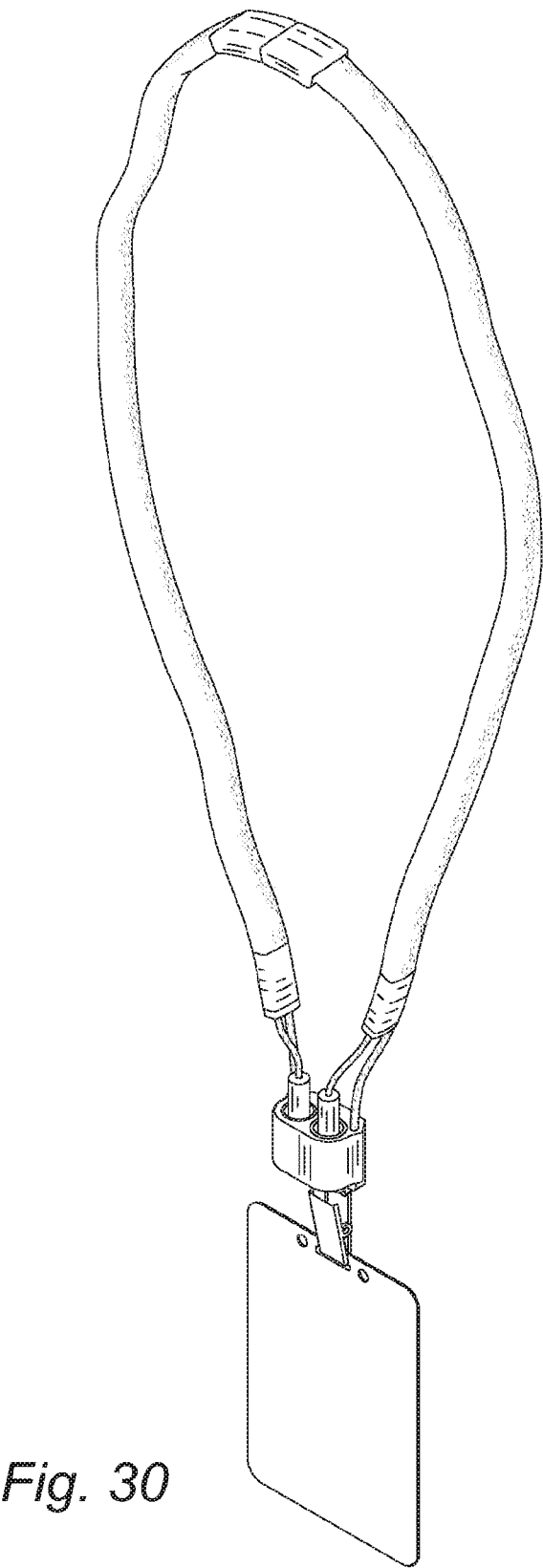
FIG. 30 shows a drawing of the lanyard.

Referring now to FIGS. 15 through 30, additional drawings of the lanyard 10 are shown. Although not numbered for clarity, these contain the same structures discussed above and are understood to function in like manner. FIG. 15 shows a perspective view of a lanyard attached to a pair of glasses with one of the retractable sheaths partially retracted. FIG. 16 shows a top view of the lanyard and glasses. FIG. 17 shows a bottom view of the lanyard and glasses. FIG. 18 shows a back view of the lanyard and glasses. FIG. 19 shows a front view of the lanyard and glasses. FIG. 20 shows a right view of the lanyard and glasses. FIG. 21 shows a left view of the lanyard and glasses. FIG. 22 shows a perspective view of the lanyard and glasses with the retractable sleeve extended. FIG. 23 shows a perspective view of a lanyard attached to an ID badge with one of the retractable sheaths partially retracted. FIG. 24 shows a top view of the lanyard and ID badge. FIG. 25 shows a bottom view of the lanyard and ID badge. FIG. 26 shows a back view of the lanyard and ID badge. FIG. 27 shows a front view of the lanyard and ID badge. FIG. 28 shows a right view of the lanyard and ID badge. FIG. 29 shows a left view of the lanyard and ID badge. FIG. 30 shows a perspective view of the lanyard and ID badge with the retractable sleeve extended.

The lanyard 10 provides several benefits. The lanyard 10 helps to ensure compliance with safety requirements in a workplace or other area where hazardous situations exist. In some situations, workers will spend a lengthy period of time in an area where personal protective equipment such as safety glasses and ear plugs are required. In other situations, however, a worker may frequently move between areas where such safety equipment is required and other areas where the safety equipment is detrimental. For example, a worker may frequently move between a shop or production area where safety glasses and ear plugs are required and an office area where these items may interfere with communication with other persons. In such a situation, compliance may suffer because of the inconvenience of using the protective items and the perceived risk of brief periods of time in the production environment. Rate of compliance is often correlated with ease of compliance and perceived risk.

The lanyard 10 places safety devices such as safety glasses and ear plugs within easy reach of a worker. By wearing the lanyard around their neck, a worker has constant and easy access to the safety glasses and ear plugs and suffers little inconvenience by using these items in areas where their use is required. The ear plugs are also kept clean as well as ready for use. Additionally, the lanyard prevents loss of these items and thereby increases compliance in using the safety glasses and ear plugs. Where a worker frequently moves between a shop and an office, the worker may frequently remove safety glasses or ear plugs in the office and place these on a desk or other location. When moving back to the shop, the worker may not be able to find the safety equipment and may enter the shop without them. The lanyard 10 ensures that the safety glasses and ear plugs remain with the worker and increases the likelihood that they are used when appropriate.

The lanyard 10 is also beneficial in situations where lost items are particularly problematic as they prevent loss. For example, workers in military or aerospace maintenance must often account for each tool or item which entered a work area to ensure that no item was misplaced inside of the machine being serviced. Tools or personal items which are lost or misplaced inside of a machine could cause failure of the machine. Lost items could cause mechanical failure of moving parts, blockage of fluid passages, shorts between electrical terminals, etc. Thus, service of sensitive or high importance machines such as in military or aerospace often requires that every tool or personal item be accounted for. If a tool or a personal item is lost, a search must be made until it is found; even if this means disassembly and reassembly of the machine. The lanyard 10 helps to ensure that safety glasses and ear plugs are not lost while working as these items are attached to the lanyard and suspended around the worker's neck. If the lanyard happens to fall off of the worker's neck, it is a larger item which is unlikely to fall into a confined space and which is much more easily retrieved than a small item such as an individual ear plug.

There is thus disclosed an improved lanyard for carrying personal safety equipment. The above description of illustrated examples of the present invention, including what is described in the Abstract, are not intended to be exhaustive or to be limitation to the precise forms disclosed. While specific embodiments of, and examples for, the invention are described herein for illustrative purposes, various changes may be made to the present invention without departing from the scope of the claims.

What is claimed is:

1. A device comprising:
   an earplug, the earplug having a distal sound blocking end which is configured for placement in an ear to block sound and a proximal end;
   an earplug cord, the earplug cord having a first end and a second end;
   an earplug receiver body, the earplug receiver body having an earplug receptacle, an earplug cord hole, and a mounting hole;
   wherein the first end of the earplug cord is attached to the proximal end of the earplug;
   wherein the second end of the earplug cord is secured within the earplug cord hole to thereby attach the earplug cord to the earplug receiver body;
   wherein the distal sound blocking end of the earplug is disposed in the earplug receptacle to store the earplug; and
   wherein the mounting hole connects the earplug receiver body to an eyeglasses temple by receiving the eyeglasses temple through the mounting hole; and
   wherein the receiver body further comprises a second mounting hole and wherein the device further comprises a lanyard having an end which is secured within the second mounting hole to thereby attach the lanyard to the receiver body.

2. The device of claim 1, wherein the earplug receptacle is held in a fixed orientation relative to the eyeglasses temple.

3. The device of claim 1, wherein the earplug receiver body is a unitary body.

4. A device comprising:
   eyeglasses, the eyeglasses comprising an eyeglass temple;
   an earplug, the earplug having a distal sound blocking end which is configured for placement in an ear to block sound and a proximal end;
   an earplug receiver body, the earplug receiver body having an earplug receptacle and a mounting hole;
   a lanyard having a first end;
   wherein the distal sound blocking end of the earplug is disposed in the earplug receptacle to store the earplug; and
   wherein the eyeglass temple is disposed in the earplug receiver body mounting hole such that the earplug receiver body extends around the eyeglass temple and is attached to the eyeglass temple; and
   wherein the earplug receiver body further comprises a second mounting hole, and wherein the first end of the lanyard is secured within the second mounting hole to thereby attach the earplug receiver body to the lanyard.

5. The device of claim 4, further comprising an earplug cord, the earplug cord having a first end and a second end;
   wherein the first end of the earplug cord is attached to the proximal end of the earplug; and
   wherein the second end of the earplug cord is attached to the earplug receiver body.

6. The device of claim 5, wherein the earplug receiver body further comprises an earplug cord hole, and wherein the second end of the earplug cord is disposed in the earplug cord hole to thereby attach the earplug cord to the earplug receiver body.

7. The device of claim 4, wherein the eyeglass temple passes through the earplug receiver body mounting hole and extends from the earplug receiver body.

8. The device of claim 4, wherein the earplug receiver body is a unitary body comprising the earplug receptacle and the mounting hole.

9. The device of claim 4, wherein the earplug receiver body is a unitary elastomeric body.

10. The device of claim 4, wherein the earplug receptacle is in a fixed orientation relative to the first eyeglass temple.

11. The device of claim 4, wherein the earplug is disposed adjacent the first eyeglass temple.

12. A device comprising:
    eyeglasses, the eyeglasses comprising a first eyeglass temple;
    an earplug, the earplug having a distal sound blocking end which is configured for placement in an ear to block sound and a proximal end;
    an earplug receiver body, the earplug receiver body having an earplug receptacle formed therein and a mounting hole formed therein;
    an earplug cord, the earplug cord having a first end and a second end;
    wherein the earplug receiver body comprises an earplug cord hole;
    wherein the first end of the earplug cord is attached to the proximal end of the earplug; and
    wherein the second end of the earplug cord is disposed in the earplug cord hole to thereby attach the earplug to the earplug receiver body
    wherein the distal sound blocking end of the earplug is disposed in the earplug receptacle to store the earplug; and
    wherein the first eyeglass temple is disposed in the earplug receiver body mounting hole such that the earplug receiver body extends around the eyeglass temple and such that the earplug is disposed adjacent the first eyeglass temple.

13. The device of claim 12, wherein the wherein the eyeglasses further comprises a second eyeglass temple, and wherein the device further comprises:
    a second earplug, the second earplug having a distal sound blocking end which is configured for placement in an ear to block sound and a proximal end;
    a second earplug receiver body, the second earplug receiver body comprising a second earplug receptacle formed therein and a second mounting hole formed therein;

wherein the distal sound blocking end of the second earplug is disposed in the second earplug receptacle to store the second earplug; and wherein the second eyeglass temple is disposed in the second mounting hole such that the second earplug receiver body extends around the second eyeglass temple.

14. The device of claim 12, wherein the earplug receiver body is a unitary body comprising the earplug receptacle and the mounting hole.

15. The device of claim 12, wherein the first eyeglass temple passes through the earplug receiver body such that the earplug receiver body is attached near a middle of the first eyeglass temple and such that the earplug is disposed adjacent a middle of the first eyeglass temple.

16. The device of claim 12, wherein the device further comprises an elongate lanyard having a first end, and wherein the first end of the lanyard is attached to the earplug receiver body.

17. The device of claim 12, wherein the earplug receptacle is in a fixed orientation relative to the first eyeglass temple.

18. A device comprising:
a first earplug, the first earplug having a distal sound blocking end which is configured for placement in an ear to block sound and a proximal end;
a second earplug, the second earplug having a distal sound blocking end which is configured for placement in an ear to block sound and a proximal end;
a first earplug cord, the first earplug cord having a first end and a second end;
a second earplug cord, the second earplug cord having a first end and a second end;
an earplug receiver body, the earplug receiver body comprising a first earplug receptacle, a first earplug cord hole, a second earplug receptacle, a second earplug cord hole, and a mounting hole;
wherein the first end of the first earplug cord is attached to the proximal end of the first earplug;
wherein the second end of the first earplug cord is secured within the first earplug cord hole to thereby attach the first earplug cord to the earplug receiver body;
wherein the distal sound blocking end of the first earplug is disposed in the earplug receptacle to store the earplug;
wherein the first end of the second earplug cord is attached to the proximal end of the second earplug;
wherein the second end of the second earplug cord is secured within the second earplug cord hole to thereby attach the second earplug cord to the earplug receiver body; and
wherein the distal sound blocking end of the second earplug is disposed in the second earplug receptacle to store the second earplug; and
wherein the mounting hole connects the earplug receiver body to a personal item.

* * * * *